(12) United States Patent
Koch

(10) Patent No.: US 6,367,472 B1
(45) Date of Patent: Apr. 9, 2002

(54) RESPIRATION HUMIDIFIER

(75) Inventor: Jochim Koch, Ratzeburg (DE)

(73) Assignee: Dragerwerk Aktiengesellschaft (DE)

( * ) Notice: Subject to any disclaimer, the term of this patent is extended or adjusted under 35 U.S.C. 154(b) by 452 days.

(21) Appl. No.: 08/796,513

(22) Filed: Feb. 6, 1997

(30) Foreign Application Priority Data

May 29, 1996 (DE) ........................................ 196 21 541

(51) Int. Cl.⁷ ............................................ A61M 15/00
(52) U.S. Cl. ............................ 128/203.12; 128/203.16; 128/204.13; 128/204.17
(58) Field of Search ...................... 128/203.12, 205.12, 128/203.16, 203.17, 200.13, 201.13, 203.27, 204.17, 204.13; 95/54; 210/323

(56) References Cited

U.S. PATENT DOCUMENTS

| | | | | |
|---|---|---|---|---|
| 3,695,267 A | * | 10/1972 | Hirtz et al. ............ | 128/203.17 |
| 3,871,373 A | | 3/1975 | Jackson ................ | 128/203.12 |
| 4,201,825 A | * | 5/1980 | Ebneth ................. | 428/263 |
| 4,367,734 A | * | 1/1983 | Benthin ................ | 128/203.16 |
| 4,381,267 A | * | 4/1983 | Jackson ................ | 128/204.13 |
| 4,587,016 A | * | 5/1986 | Sumiyoshi .............. | 210/323 |
| 4,771,770 A | * | 9/1988 | Artemenko et al. ... | 128/201.13 |
| 4,774,032 A | * | 9/1988 | Coates et al. .......... | 128/204.13 |
| 4,825,863 A | * | 5/1989 | Dittmar et al. ........ | 128/204.17 |
| 4,829,997 A | * | 5/1989 | Douwens et al. ...... | 128/201.13 |
| 4,844,059 A | * | 7/1989 | Koch .................... | 128/205.12 |
| 5,143,060 A | * | 9/1992 | Smith .................... | 128/204.17 |
| 5,356,459 A | * | 10/1994 | Bikson et al. .......... | 95/54 |
| 5,380,433 A | * | 1/1995 | Etienne et al. | |
| 5,383,448 A | * | 1/1995 | Tkatchouk et al. .... | 128/205.12 |
| 5,462,048 A | * | 10/1995 | Lambert et al. ....... | 128/203.16 |
| 5,468,384 A | * | 11/1995 | Garcera et al. ......... | 210/232 |
| 5,577,494 A | * | 11/1996 | Kuypers et al. ....... | 128/204.13 |
| 5,617,913 A | * | 4/1997 | DeGregoria et al. ... | 128/201.13 |
| 5,647,344 A | * | 7/1997 | Turnbull ................. | 128/205.12 |
| 5,657,750 A | * | 8/1997 | Coleman ................ | 128/204.13 |

FOREIGN PATENT DOCUMENTS

| | | | | |
|---|---|---|---|---|
| GB | 2223694 A | * | 4/1990 | 128/204.17 |
| WO | WO94/02192 | * | 2/1994 | 128/203.16 |

* cited by examiner

Primary Examiner—John G. Weiss
Assistant Examiner—V. Srivastava
(74) Attorney, Agent, or Firm—McGlew and Tuttle, P.C.

(57) ABSTRACT

An improved, compact and low-maintenance respiration humidifier of a simple design is proposed, which has an outer jacket with a water feed as well as a breathing gas feed line and breathing gas drain line and contains a bundle of hydrophobic hollow fibers. The breathing gas feed line and the breathing gas drain line are in a gas flow connection with the interior of the hollow fibers. The hollow fibers preferably include polytetrafluoroethylene (PTFE) and have structure for electrical heating on their outer, water-side circumferential surface.

19 Claims, 1 Drawing Sheet

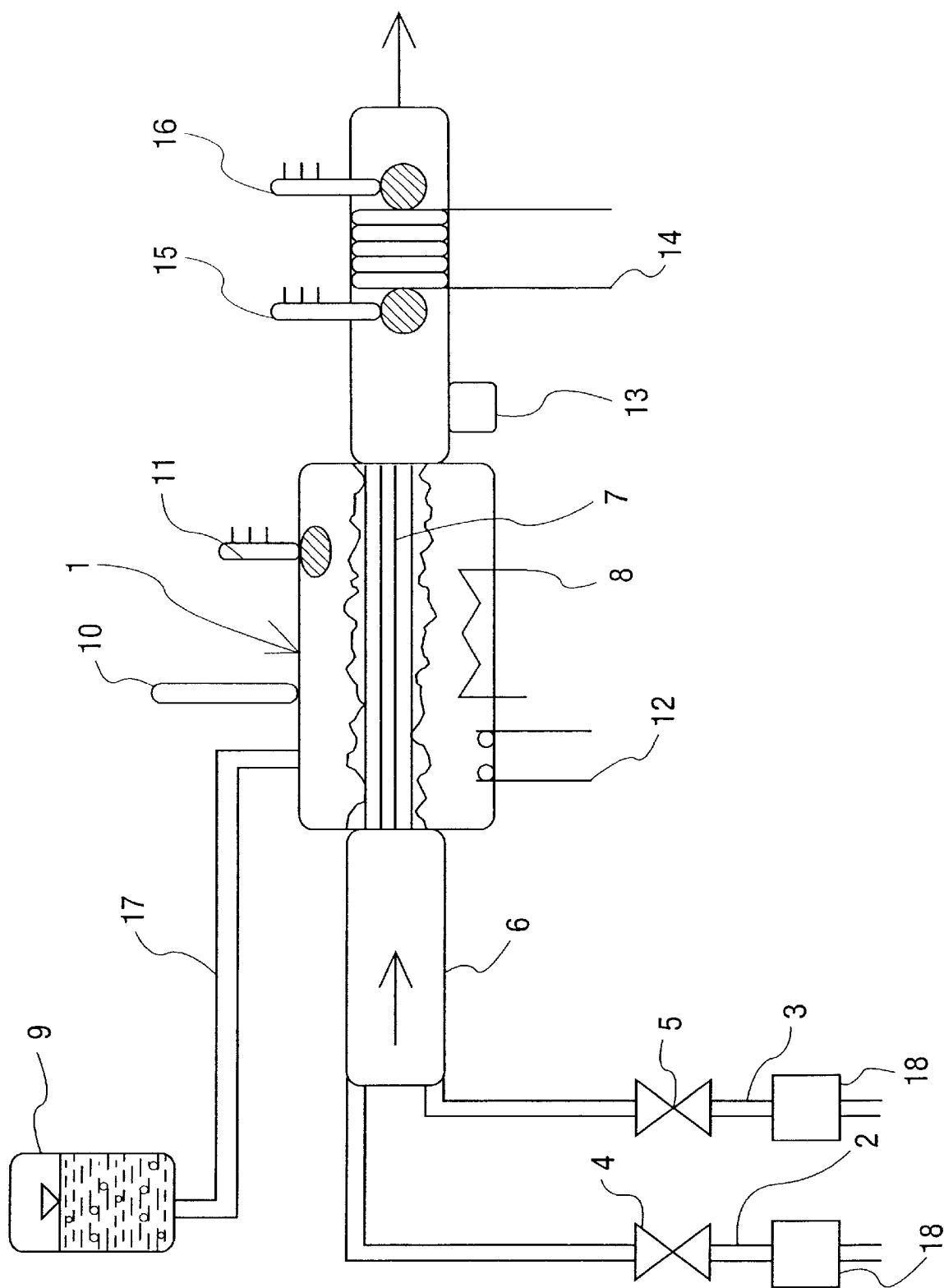

RESPIRATION HUMIDIFIER

FIELD OF THE INVENTION

The present invention pertains to a respiration humidifier with an outer jacket, a water feed, a breathing feed line and a breathing gas drain line. A bundle of hydrophobic hollow fibers made of a material that is permeable to water vapor but is impermeable to water is positioned inside the outer jacket. The breathing gas feed line and breathing gas drain line are in flow connection with the interior of the hollow fibers.

BACKGROUND OF THE INVENTION

Respiration humidifiers are used to humidify the inspiratory air of respirators to physiological values and to optionally beat it. Such devices, which operate according to various principles, are arranged, in general, separated from the respirator.

One drawback of the separate arrangement for the user is the lack of clarity of handling, due, among other things, to the large number of different tubing and connections. If a humidifier is integrated within the respirator, the diversity of accessories and ultimately the overall costs can be reduced for the manufacturer, because a completely equipped respirator is offered.

A respiration humidifier of this class has been known from U.S. Pat. No. 3,871,373. One drawback of this respiration humidifier is the relative size as well as the additionally necessary components, such as pumps, feed and drain lines.

SUMMARY AND OBJECTS OF THE INVENTION

The object of the present invention is to propose an improved, compact and low-maintenance respiration humidifier of a simple design. The object is accomplished by means of hollow fibers having means for electrical heating on their outer circumferential surface.

One essential advantage of the present invention is that due to the compact, modular design, the respiration humidifier according to the present invention can be directly integrated in the inspiratory line of the respirator. Another advantage of the present invention arises from the fact that hygienically objectionable contamination of the breathing air can be avoided due to the closed water system. For feeding in water, a water bag containing sterile water is simply connected, and the static pressure of this bag fills the module according to the present invention with water.

For example, an intubation kit commonly employed in hospital practice may be used as the supply line. The water connection to the modular respiration humidifier according to the present invention can be designed such that a bacteria filter is arranged at the inlet, so that microorganisms cannot enter even if the water bag is not connected.

The respiration humidifier according to the present invention is designed as follows. A bundle of hollow fibers arranged essentially in parallel, preferably made of one of polytetrafluoroethylene (PTFE), polyurethane, polysulfone, and porous sinted glass, is located in an outer jacket, e.g., one made of a laminated plastic, the length and the diameter of the fibers being selected to be such that a water vapor-permeable area of about 500 to 800 $cm^2$ is available in the circumferential area in the case of a corresponding number of fibers. The porous sintered glass can be hydrophobized with silicone. In the case of a fiber diameter of 1 to 2 mm, about 200 fibers with a length of about 65 mm are needed in order not to generate an excessively high flow resistance, and in order to obtain the most compact design possible with the desired humidifying capacity. A suitable flow expansion, which is directly in flow connection with a breathing gas feed line and with a breathing gas drain line into and out of the respiration humidifier, is located in the beginning and end areas of the hollow fibers. The water-filled outer area around the hollow fibers, which is in flow connection with the water reservoir via the water feed of the module, is located around the hollow fibers, and is closed by the outer, laminated jacket.

The hollow fibers themselves consist of hydrophobic or hydrophobically coated membranes, preferably ones made of PTFE, which let water through in the form of water vapor, but retain liquid water under the given conditions of use. After the water reservoir has been connected and the volume around the hollow fibers has been filled with water due to the static pressure, the entrapped air can flow out of the respiration humidifier via a separate ventilation, e.g., one made of porous PTFE, unless the hydrophobic hollow fibers exert a sufficient ventilating action themselves. The hollow fibers used make it possible to passively establish a nearly constant humidification of the air fed in the range of 90% to 100% relative humidity over the broad range of flow conditions. This means that the flow of gas is always humidified uniformly in continuous operation and in intermittent operation. It is essential for the present invention that the heater is arranged directly around the hollow fibers in the water bath in the jacket of the respiration humidifier, i.e., it is integrated in the humidifier module. It was found that the heat must be fed in as close as possible to the area in which the evaporation is generated. The evaporation takes place in this case on the inside of the hollow fibers on the gas/air side.

The basic objective of the present invention is to operate all hollow fibers at the same temperature in order to obtain an extensively uniform breathing gas temperature and humidity over the entire cross section of the humidifier module. Only this can guarantee an optimal utilization of every individual hollow fiber in terms of the release of humidity and heat. Individual hollow fibers might otherwise be too cold and would have an insufficient humidification capacity, whereas others would be too warm and thus they would lead to excessive humidification capacity, as a result of which the humidity would again precipitate as a condensate. Each hollow fiber of the bundle is directly heated electrically according to the present invention. This can be done in the following ways. Individual resistor wires are wound around the hollow fibers and in the longitudinal direction, or they are printed on or applied as strips or films, and, as an alternative and preferably, the hollow fibers are preferably coated from the outside by vapor deposition with a metal used as a resistor heater, and are provided with corresponding current connections. According to another variant of the preparation, the hollow fibers would be arranged on a heating foil in parallel and next to each other. The strip thus equipped would then be rolled up, so that a hollow fiber bundle with direct heating of at least part of the opposite circumferential surface areas of the hollow fibers is formed. The system is operated in practice such that a temperature range of about 40° C. to 45° C. is not exceeded, so that short-term bursts of hot gas, which are sometimes possible in prior-art humidifier systems, are ruled out. For a precautionary disinfection or sterilization, the entire humidifier module can be briefly heated by the integrated heater to a desired temperature, e.g., to 134° C. for 3 minutes.

A temperature sensor may be introduced into the water bath for a desired temperature control. This may also be used at the same time to recognize lack of water and a possible overheating that may occur as a result. A possibly desired heater of the airway tubes with temperature control can be operated independently from the humidifier module. Setting of the desired humidity can be performed with this tube heater, which was also used in the prior art. If, e.g., the temperature is higher at the end of the inspiration tube than at the beginning, the relative humidity is reduced. The setting of the desired breathing gas temperature may also be performed directly from the respirator, and the measured values are indicated there. The control and the supply of the humidifier module with the correctly metered thermal energy may also be provided on the respirator, so that the respiration humidifier according to the present invention can also be integrated in a respirator functionally, not only due to its compact, modular design.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS In the drawings:

The sole drawing is a schematic view of the present invention.

DETAILED DESCRIPTION OF THE PREFERRED EMBODIMENT

A respiration humidifier according to the present invention was designed for the artificial respiration of adults and newborns such that it is able to deliver a sufficiently high relative humidity of at least 95% at a breathing gas temperature of 37° C. at a continuous breathing gas flow rate of 30 L/minute, corresponding to 44 mg of water per g of air, and it can briefly reach the desired humidification capacity for about one second even at a maximum flow of 180 L/minute during the intermittent artificial respiration of adults. To obtain the necessary area as a heat exchanger and for feeding in the humidity, an exchange area of 500 to 800 $cm^2$ of the circumferential area of the hollow fibers must be available. The smaller the fiber diameter, e.g., 1 to 2 mm, the smaller is the attainable size of the respiration humidifier. The smaller the fiber diameter selected, the better is the heat transfer from the hollow fibers to the breathing gas, but the overall flow resistance increases. According to the ISO 8185 standard, the maximum allowable resistance for respiration humidifiers is 2 mbar at 60 L/minute. This resistance is just reached with a fiber diameter of 1.25 mm and 200 fibers having a length of about 65 mm, so that the smallest practical volume is obtained for a humidifier according to the present invention, which does not exceed the maximum allowable flow resistance.

The necessary heating capacity of the humidifiers according to the present invention must deliver the necessary heat of evaporation. This requires a heating capacity of about 60 W. In addition, the breathing gas must also be heated to the desired breathing gas temperature of about 37° C. from an ambient temperature of about 25° C. This requires about 10 W.

Another 30 W are needed due to heat losses via the housing, to the environment, for the heating of the water and of the materials, so that the humidifier must be supplied with a total amount of about 100 W of electricity. For safety engineering reasons, the heater is operated with low voltage, 10 to 48 V. The temperature of the water within the humidifier module is measured either via an individual temperature sensor, via a temperature sensor integrated in the heating foil or the heating strips or the heating wires, or by determining the temperature by measuring the heating resistance. The water temperature is preferably used as the control input variable to control the inspiration gas temperature behind the humidifier module. If individual hollow fibers develop leaks during the operation, the overflow of too much water to the patient must be prevented from occurring. This may be done, e.g., by limiting the feed of water to the humidifier through a nozzle in the flow path. This flow limiter may be connected to a water level gauge in the outlet area of the humidifier in the form of a collection point, preferably at the lowermost point of the outlet spout, where, e.g., two electrical contacts can generate an impulse for an alarm because of a larger amount of water and may optionally close a corresponding valve in the water feed line. The function of the contacts may alternatively be triggered by a float.

Humidifiers according to the present invention are also suitable for humidification and heating in the open care of premature babies, where care devices correspondingly covered with foils, hoods or similar means can support and favorably affect a microclimate generated by the release of humidity by the infant by actively supplying humidity by humidifiers according to the present invention. For example, air can be drawn in from the environment by means of a fan and its temperature and humidity can be conditioned via the modular humidifier and be fed into the care area. A bacteria filter may be arranged in front of the fan in order to protect the patient from microorganisms. As an alternative, the fan may be omitted if compressed air from a central supply system or from gas cylinders is used. The metering can be set with constant volume flow, and optionally mixed with oxygen at a desired concentration. Depending on the intended use and the dimensioning of the feed of breathing gas, it is also possible to expose only part of the breathing gas to a humidifier according to the present invention if it is arranged in the form of a bypass in parallel to the rest of the gas flow, i.e., it humidifies and warms only a partial flow.

The only FIGURE schematically shows the arrangement of a respiration humidifier 1 according to the present invention as a compact, modular element of a respirator device. Air and oxygen under pressure, or force by a fan 18, are fed via two gas supply lines 2, 3 via valves 4, 5 to a respirator 6 with a suitable mixing means belonging to it as well as a corresponding metering unit. The breathing gas enters the respiration humidifier 1 via a connection line, not shown. The respiration humidifier contains, e.g., 200 hydrophobic hollow fibers made of PTFE, which are arranged as a parallel bundle and whose interior spaces are in a flow connection with the breathing gas feed line and breathing gas drain line of the respiration humidifier 1. The heater 8, indicated schematically, is designed such that the hollow fibers 7 are heated directly and individually in order to bring about the most favorable humidification and heating of the breathing air possible. The water is fed via the line 17 based on the static pressure from a water reservoir 9, e.g., in the form of a tube or bag, into a jacket surrounding the water space, so that the hollow fibers 7 are surrounded by water on the outside. An opening 10 for the air being displaced must be present for venting during the filling in of the water. This opening may be designed simply as a porous PTFE surface with corresponding permeability. The water temperature is measured via a suitable temperature sensor 11, and the heater 8 can thus be controlled. A possible lack of water would additionally be able to be detected via this measuring and control circuit. As an alternative, it would be possible to provide a sensor 12, e.g., in the form of a switching element actuated by a float. A collection point 13 for excess water is advantageously located at the gas outlet from the humidifier for the case of a hollow fiber 7 developing a leak and a corresponding excess of water entering the breathing gas line. The desired humidity of the breathing gas can be set by means of a heater 14 arranged in the downstream airway tube and temperature sensors 15, 16 arranged upstream and downstream. A temperature that is higher at the end of the inspiration tube than at the beginning leads, e.g., to a reduced relative humidity of the air. The humidified breathing air finally reaches the patient in the direction of the arrow via a mouthpiece or a tube.

Essential advantages of the present invention result from the compact design, from the possibility of integration in existing respirator systems, from the satisfactory hygienic properties due to the closed water system, and from a simple design without a pump and with fewer tubes in comparison with usual systems.

While specific embodiments of the invention have been shown and described in detail to illustrate the application of the principles of the invention, it will be understood that the invention may be embodied otherwise without departing from such principles.

What is claimed is:

1. A respiration humidifier comprising:
   an outer jacket;
   a plurality of hydrophobic hollow fibers positioned in said outer jacket and made of a material permeable to water vapor but impermeable to liquid water;
   a water feed connected to said outer jacket;
   a breathing feed line and a breathing gas drain line in flow connection with an interior of said hollow fibers;
   electrical heating means for electrical heating said hollow fibers on their outer circumferential surface.

2. A respiration humidifier in accordance with claim 1, wherein:
   said hollow fibers are formed from one of polytetrafluorethylene (PTFE), polyurethane, polysulfone, and porous sintered glass.

3. A respiration humidifier in accordance with claim 2, wherein:
   said porous sintered glass is hydrophobized with silicone.

4. A respiration humidifier in accordance with claim 1 wherein:
   each of said hollow fibers are provided with one heating wires and an electrically heatable layer of material.

5. A respiration humidifier in accordance with claim 4, wherein:
   said heatable layer is formed of metal and is applied by vapor deposition.

6. A respiration humidifier in accordance with claim 2, wherein:
   each of said hollow fibers are provided with one of heating wires and an electrically heatable layer of material.

7. A respiration humidifier in accordance with claim 6, wherein:
   said heatable layer is formed of metal and is applied by vapor deposition.

8. A respiration humidifier in accordance with claim 1, wherein:
   said water feed is directly connected to a water reservoir emptying by static pressure.

9. A respiration humidifier in accordance with claim 1, wherein:
   a surface of said hollow fibers acts as a water vapor passage surface and has a magnitude of approximately 500 to 800 $cm^2$.

10. A respiration humidifier in accordance with claim 1, wherein:
    air to be humidified is fed in from a surrounding environment by one of a fan means and by excess pressure from a gas reservoir.

11. A respiration humidifier in accordance with claim 10, wherein:
    said gas reservoir includes oxygen.

12. A respiration humidifier comprising:
    an outer jacket;
    a plurality of hydrophobic hollow fibers positioned in said outer jacket and made of a material permeable to water vapor but impermeable to liquid water;
    a water feed connected to said outer jacket and in communication with a space between an outside of said fibers and an inside of said outer jacket;
    a breathing feed line and a breathing gas drain line in flow connection with an interior of said hollow fibers;
    heating means for directly and substantially evenly heating an outer circumferential surface of said hollow fibers.

13. A respiration humidifier in accordance with claim 1, wherein:
    said heating means is in direct contact with said outer circumferential surface of said hollow fibers.

14. A respiration humidifier in accordance with claim 12, wherein:
    said heating means is in direct contact around said outer circumferential surface of said hollow fibers.

15. A respiration humidifier in accordance with claim 14, wherein:
    said hollow fibers are formed from one of polytetrafluoroethylene (PTFE), polyurethane, polysulfone, and porous sintered glass.

16. A respiration humidifier in accordance with claim 15, wherein:
    said porous sintered glass is hydrophobized with silicone.

17. A respiration humidifier in accordance with claim 16, wherein:
    each of said hollow fibers are provided with heating wires as said heating means.

18. A respiration humidifier in accordance with claim 16, wherein:
    each of said hollow fibers are provided with an electrically heatable layer of material as said heating means.

19. A respiration humidifier in accordance with claim 18, wherein:
    said heatable layer is formed of metal and is applied by vapor deposition.

* * * * *